US011464850B2

(12) United States Patent
Huang et al.

(10) Patent No.: US 11,464,850 B2
(45) Date of Patent: Oct. 11, 2022

(54) RECOMBINANT RSV ANTIGENS, NUCLEIC ACID MOLECULES ENCODING THE ANTIGENS, AND VACCINE COMPOSITIONS COMPRISING THE SAME

(71) Applicant: National Taiwan University, Taipei (TW)

(72) Inventors: Limin Huang, Taipei (TW); Jenmin Huang, Hsinchu (TW)

(73) Assignee: National Taiwan University, Taipei (TW)

( * ) Notice: Subject to any disclaimer, the term of this patent is extended or adjusted under 35 U.S.C. 154(b) by 422 days.

(21) Appl. No.: 16/462,757

(22) PCT Filed: Nov. 22, 2017

(86) PCT No.: PCT/CN2017/112361
§ 371 (c)(1),
(2) Date: May 21, 2019

(87) PCT Pub. No.: WO2018/095330
PCT Pub. Date: May 31, 2018

(65) Prior Publication Data

US 2019/0314491 A1 Oct. 17, 2019

Related U.S. Application Data

(60) Provisional application No. 62/425,078, filed on Nov. 22, 2016.

(51) Int. Cl.

| | |
|---|---|
| ***A61K 39/155*** | (2006.01) |
| ***C07K 14/135*** | (2006.01) |
| ***C12N 15/85*** | (2006.01) |

(52) U.S. Cl.
CPC .......... *A61K 39/155* (2013.01); *C07K 14/135* (2013.01); *C12N 15/85* (2013.01); *C12N 2015/8518* (2013.01); *C12N 2760/18534* (2013.01); *C12N 2760/18541* (2013.01); *C12N 2800/22* (2013.01)

(58) Field of Classification Search
None
See application file for complete search history.

(56) References Cited

U.S. PATENT DOCUMENTS

2015/0366960 A1* 12/2015 Ulbrandt ................ A61P 31/14
424/186.1

FOREIGN PATENT DOCUMENTS

WO WO-2015048149 A1 * 4/2015 .......... A61K 39/155

OTHER PUBLICATIONS

Baker et al., Molecular CellVol 3, pp. 309-319 (Year: 1999).*
Ravin et al., Vaccine 33 (2015) 3392-3397 (Year: 2015).*

* cited by examiner

*Primary Examiner* — Shanon A. Foley
*Assistant Examiner* — Myron G Hill
(74) *Attorney, Agent, or Firm* — Fox Rothschild LLP

(57) ABSTRACT

Provided is an antigen including a recombinant respiratory syncytial virus (RSV) F protein, wherein the recombinant RSV F protein includes an antigenic region flanked with an HRN region and an HRC region, and the antigenic region includes one or more antigenic sites selected from the group consisting of site Ø, site II, and site IV. The present disclosure also provides a nucleic acid molecule encoding the antigen and a vaccine composition including the antigen for eliciting an immune response against RSV.

19 Claims, 11 Drawing Sheets

Specification includes a Sequence Listing.

RECOMBINANT RSV ANTIGENS, NUCLEIC ACID MOLECULES ENCODING THE ANTIGENS, AND VACCINE COMPOSITIONS COMPRISING THE SAME

CROSS-REFERENCE TO RELATED APPLICATIONS

The present application is a U.S. national stage application, filed under 35 U.S.C. § 371, of PCT/CN2017/112361 filed Nov. 22, 2017, which claims the priority of U.S. Provisional Application Ser. No. 62/425,078 filed on Nov. 22, 2016 which is herein incorporated by reference in its-their entirety.

SEQUENCE LISTING

The instant application contains a Sequence Listing which has been submitted electronically in ASCII format and is hereby incorporated by reference in its entirety. Said ASCII copy, created on May 17, 2022, is named 068293-643N01US_Sequence_List.txt and is 14,891 bytes in size.

BACKGROUND

1. Technical Field

The present disclosure relates to antigens, nucleic acid molecules, and vaccine compositions for elicitation of an immune response, and more particularly for eliciting an immune response against a respiratory syncytial virus (RSV).

2. Description of Associated Art

RSV has been recognized as the most common cause of lower respiratory tract infections in infants and young children. According to the report from World Health Organization, RSV is responsible for an estimated 199,000 deaths annually worldwide, and 99% of which occur in developing countries (Nair, H., et al., 2011). RSV can also infect and cause diseases in people of all ages, most severely in the elderly and in immuno-compromised individuals. Most children are infected at least once by age 2 and continue to be re-infected throughout life possibly due to incomplete immunity to RSV (Hall, C. B., et al., 1991).

Despite the burden of diseases caused by RSV, currently available prophylactic and therapeutic methods in RSV are very limited. For example, a humanized monoclonal antibody, palivizumab (SYNAGIS®; MedImmune, Inc.), comprises 95% human antibody sequence and 5% murine antibody sequences. Palivizumab can treat lower respiratory tract disease caused by RSV by binding to an epitope in the A antigenic site of the F subunit of RSV. However, palivizumab is licensed only for use in high-risk infants. In addition, it has been shown that the antiviral agent, ribavirin, has a therapeutic effect on RSV pneumonia and bronchiolitis, while ribavirin is used to treat RSV infection only in the pediatric population. Furthermore, ribavirin is accompanied by many side effects, e.g., insomnia, dyspnea, headache, nausea, muscle pains, emotional lability, hemolytic anemia, decreased hemoglobin, allergic reactions and liver problems. Moreover, ribavirin is not recommended for pregnant women due to its potential risk to the baby.

The immune effect of formalin-inactivated RSV (FIRSV) vaccine on infants and young children was evaluated in the late 1960s. Although FIRSV vaccine elicits high levels of antibodies in serum, it failed to prevent or treat the disease caused by RSV. On the contrary, those who had been received FIRSV vaccine during early infancy experienced more serious lower respiratory tract disease upon subsequent re-infection with RSV than unvaccinated individuals. Also, the current study revealed that FIRSV induced prominent alveolitis and perivasculitis in the lungs of RSV challenged mice.

A number of studies have been conducted for the development of RSV vaccines, including virus like particles (VLPs), subunits, and live-attenuated vaccines. Nevertheless, there is still no licensed vaccine against RSV infections. Due to a tremendous disease burden and limited prophylactic method, the demand for a safe and effective RSV vaccine is now greater than ever.

SUMMARY

In view of the foregoing, the present disclosure provides an antigen comprising a recombinant respiratory syncytial virus (RSV) F protein to mimic the natural trimeric conformation of the RSV F protein.

The recombinant RSV F protein comprises an antigenic region flanked with an N-terminal heptad repeat (HRN) region and a C-terminal heptad repeat (HRC) region, wherein the antigenic region comprises one or more antigenic sites selected from the group consisting of site Ø, site II, and site IV, provided that if the antigenic region comprises more than one antigenic sites, then the antigenic sites are linked to each other by a linker, and the linker, on each occurrence, independently consists of 2 to 20 amino acids.

In an embodiment of the present disclosure, the antigenic region comprises site Ø, site II, and site IV. In another embodiment of the present disclosure, the HRN region is directly linked to site Ø, and the HRC region is linked to site IV by the linker.

According to a further aspect of the present disclosure, the present disclosure provides a nucleic acid molecule encoding the recombinant RSV F antigen described above.

According to another aspect of the present disclosure, the present disclosure provides a vaccine composition comprising an effective amount of the antigen or the nucleic acid molecule described above.

In another embodiment of the present disclosure, the vaccine composition comprising an effective amount of one or more of the antigens described above and a nucleic acid molecule or a plasmid encoding or expressing the antigen is administered to a subject in need thereof under a condition sufficient to prevent or ameliorate an RSV infection in the subject. The vaccine composition is administered in an amount sufficient to elicit an immune response against an RSV antigen, such as RSV F protein, in the subject.

The present disclosure provides a recombinant RSV F protein and a nucleic acid molecule encoding the recombinant RSV F protein. Also, the present disclosure provides a vaccine composition comprising an effective amount of the antigen or the nucleic acid molecule. The antigen, nucleic acid molecule and vaccine composition of the present disclosure can induce antibody responses specific for RSV and protect the subject from RSV infection without causing an adverse effect. Further, compared with the wild-type RSV F protein, the recombinant RSV F protein of the present disclosure is shorter in length and can result in a better expression level. As such, the antigen, nucleic acid molecule and vaccine composition of the present disclosure are relatively easy in mass production and more helpful in increasing the specificity of antibody identification and avoiding unnecessary reactions such as allergy.

BRIEF DESCRIPTION OF THE DRAWINGS

The present disclosure can be more fully understood by reading the following detailed description of the embodiments, with reference made to the accompanying drawings, wherein:

FIGS. 2A, 2C, 2E, and 2G show Coomassie blue staining of purified HRØ24, HRØ, HRØ-3Ø recombinant proteins, and HBc, respectively; FIGS. 2B, 2D, and 2F show Western blotting of purified HRØ24, HRØ, and HRØ-3Ø recombinant proteins using anti-His antibody, respectively; FIG. 2H shows Western blotting of purified HBc using rabbit polyclonal anti-HBc antibody; and FIG. 2I shows Western blotting of purified HBc and HRØ24 recombinant proteins using mouse monoclonal anti-RSV antibody, respectively.

FIGS. 5A, 5B, 5C, and 5E show HRØ24-specific total IgG, IgG1, IgG2a and IgA responses measured from the serum, respectively; and FIG. 5D shows HRØ24-specific secretary IgA (sIgA) response detected from the BALF.

DETAILED DESCRIPTION OF THE EMBODIMENTS

Figures 1A, 1B, 1C:
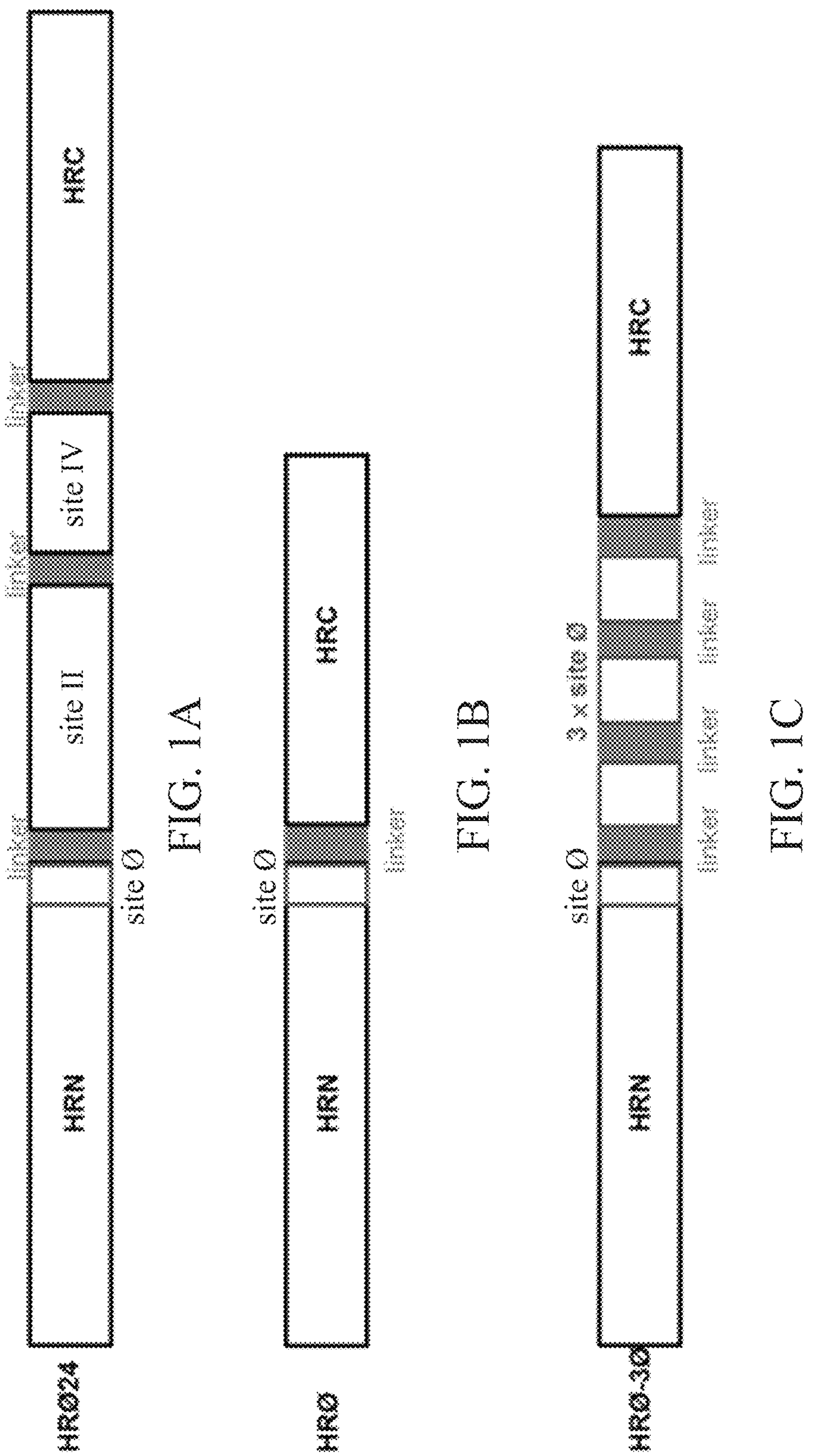
FIGS. 1A-1C show the schematic diagrams of HRØ24, HRØ, and HRØ-3Ø recombinant proteins, respectively.

The following examples are used to exemplify the present disclosure. A person of ordinary skills in the art can conceive the other advantages of the present disclosure, based on the specification of the present disclosure. The present disclosure can also be implemented or applied as described in different examples. It is possible to modify and/or alter the above examples for carrying out this disclosure without contravening its spirit and scope, for different aspects and applications.

As used herein, the singular forms "a," "an" and "the" include plural referents unless the context clearly dictates otherwise. Thus, for example, reference to "an antigen" includes mixtures of antigens; reference to "a pharmaceutically acceptable carrier" includes mixtures of two or more such carriers, and the like. As such, the terms "a" (or "an"), "one or more," and "at least one" can be used interchangeably herein.

Furthermore, "and/or" where used herein is to be taken as specific disclosure of the two specified features or components with or without the other. Thus, the term "and/or" used in a phrase such as "A and/or B" herein is intended to include "A and B," "A or B," "A (alone)," and "B (alone)."

The present disclosure provides an antigen comprising a recombinant RSV F protein. The recombinant RSV F protein comprises an antigenic region flanked with an HRN region and an HRC region, and the antigenic region comprises one or more antigenic sites selected from the group consisting of site Ø, site II, and site IV.

As descried herein, RSV has three surface glycoproteins, i.e., small hydrophobic (SH), attachment (G) and fusion (F), encoded by three consecutive genes (SH-G-F). The major target antigens of RSV vaccine development are RSV F and G as these are each capable of generating neutralizing antibodies as well as T cell responses. F is particularly attractive due to its considerable conservation among RSV isolates. Historically, there were two known major antigenic sites found on both the prefusion and postfusion conformations of RSV F associated with neutralizing (NT) activity. They were initially defined by binding to the murine monoclonal antibodies (mAbs) 1129 (site II) (Beeler, J. A. et al., 1989; Arbiza, J., et al., 1992) and 101F (site IV) (Wu, S. J., et al., 2007). Site II is known as the target for palivizumab which can reduce severe RSV disease in high-risk infants. McLellan et al. (McLellan, J. S., et al., 2013) isolated a mouse antibody, 5C4, which neutralized RSV potently but showed no binding to postfusion F protein. 5C4 shares these properties with two other antibodies isolated from immortalized peripheral blood mononuclear cells (PBMCs), D25 and AM22, which have been shown to neutralize RSV with 100 folds greater potency than palivizumab (McLellan, J. S., et al., 2013). D25 and AM22 target site Ø, a metastable antigenic site located on the surface of the prefusion RSV F trimer (Spits, H., et al., 2010; Beaumont, T., et al., 2012). The prefusion and postfusion crystal structures of F protein suggest that while sites II and IV are found on both structures, site Ø appear to be specific for the prefusion form (McLellan, J. S., et al., 2013).

The fusion peptide region of RSV F is located at the N terminus of the F1 subunit (Collins, P. L., et al., 1996) while the transmembrane segment contains two regions of 4,3-hydrophobic heptad repeats (HR), a sequence motif suggestive of coiled-coil structures (Chambers, P., et al., 1990; Singh, M., et al., 1999). These regions are denoted as HRN and HRC, respectively, and are separated by an intervening domain of about 270 amino acids. HRN and HRC form a trimeric hairpin-like structure, with the HRC regions packing in an antiparallel manner against the inner coiled-coil formed by HRN regions (Baker, K. A., et al., 1999).

In an embodiment of the present disclosure, the HRN region and the HRC region comprise amino acid sequences at least about 80%, 85%, 90%, 95%, 96%, 97%, 98%, or 99% identical to the amino acid sequences of SEQ ID NO: 1 (MAVSKVLHLEGEVNKIKSALLSTNKAVVSLSNGVSVLTSKVLDLKNYIDKQLLPIVNK QS) and SEQ ID NO: 2 (NFYDPLVFPSDEFDASISQVNEKINQSLAFIRKSDELLHNVNAGK) and have the same functions as SEQ ID NO: 1 and SEQ ID NO: 2, respectively. In another embodiment of the present disclosure, the antigenic site comprised in the antigenic region may be selected from the group consisting of site Ø, site II, and site IV. The site Ø, site II, and site IV comprise amino acid sequences at least about 80%, 85%, 90%, 95%, 96%, 97%, 98%, or 99% identical to the amino acid sequences of SEQ ID NO: 3 (KNYIDKQLLPIVNK), SEQ ID NO: 4 (NSELLSLINDMPITNDQKKLMSN), and SEQ ID NO: 5 (KNRGIIKTFS) and have the same functions as SEQ ID NO: 3, SEQ ID NO: 4, and SEQ ID NO: 5, respectively. In another embodiment of the present disclosure, if the antigenic region comprises more than one antigenic sites, then the antigenic sites are linked to each other by a linker, and the linker, on each occurrence, independently consists of 2 to 20 amino acids.

As used herein, the term "sequence identity" or, for example, comprising a "sequence 80% identical to" refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 80%, 85%, 90%, 95%, 97%, 98%, 99% or 100% sequence identity to any of the reference sequences described herein (see, e.g., Sequence Listing), typically where the polypeptide variant maintains at least one biological activity or function of the reference polypeptide.

In an embodiment of the present disclosure, the antigenic region comprises at least one site Ø directly linked to the HRN region.

In another embodiment of the present disclosure, the antigenic region comprises one site Ø directly linked to the HRN region and linked to the HRC region by the linker (see, e.g., FIG. 1). In yet another embodiment, the recombinant RSV F protein comprises an amino acid sequence at least about 80%, 85%, 90%, 95%, 96%, 97%, 98%, or 99% identical to the amino acid sequence of SEQ ID NO: 6 (MAVSKVLHLEGEVNKIKSALLSTNKAVVSL-SNGVSVLTSKVLDLKNYIDKQLLPIVNK QSGSGSGSEFGGSGNFYDPLVFPSDEFDA-SISQVNEKINQSLAFIRKSDELLHNVNAGKLE HIEHHHH) and has the same function as SEQ ID NO: 6.

In another embodiment of the present disclosure, the antigenic region comprises four site Ø, and one of which is directly linked to the HRN region (see, e.g., FIG. 1C). In yet another embodiment, the recombinant RSV F protein comprises an amino acid sequence at least about 80%, 85%, 90%, 95%, 96%, 97%, 98%, or 99% identical to the amino acid sequence of SEQ ID NO: 7 (MAVSKVLHLE-GEVNKIKSALLSTNKAVVSLSNGVSVLTSKVLD-LKNYIDKQLLPIVNK QSGSGSASSNIKENKC-NAAKNYIDKQLLPIVNKGGGSSNIKENKCNAAKNYI DKQLLPIV NKGGEFSNIKENKC-NAAKNYIDKQLLPIVNKKLGGSGNFYDPLVFPSDEF-DASISQVNEK INQSLAFIRKSDELLHNVNAGKLE) and has the same function as SEQ ID NO: 7.

In another embodiment of the present disclosure, the antigenic region comprises site Ø, site II, and site IV. In another embodiment of the present disclosure, the HRN region is directly linked to site Ø, and the HRC region is linked to site IV by the linker (see, e.g., FIG. 1A). In yet another embodiment, the recombinant RSV F protein comprises an amino acid sequence at least about 80%, 85%, 90%, 95%, 96%, 97%, 98%, or 99% identical to the amino acid sequence of SEQ ID NO: 8 (MAVSKVLHLE-GEVNKIKSALLSTNKAVVSLSNGVSVLTSKVLD-LKNYIDKQLLPIVNK QSGSGSN-SELLSLINDMPITNDQKKLMSNNVQIVRQGGGSCTA SNKNRGIIKTFSNGGGS GNFYDPLVFPSDEFDA-SISQVNEKINQSLAFIRKSDELLHNVNAGK) and has the same function as SEQ ID NO: 8.

In an embodiment of the present disclosure, the linker, on each occurrence, independently consists of 2 to 20 amino acids, and the linker may independently include, but not limited to, an amino acid sequence of any one of GSGS (SEQ ID NO: 38), GGGS (SEQ ID NO: 39), GGSG (SEQ ID NO: 40), SGSG (SEQ ID NO: 41) and GG (SEQ ID NO: 42).

In an embodiment of the present disclosure, the antigen specifically binds to a 5C4, a D25, or an AM22 prefusion-specific antibody.

According to a further aspect of the present disclosure, the present disclosure provides a nucleic acid molecule encoding the antigen described above.

In an embodiment of the present disclosure, the nucleic acid molecule is codon optimized for expression in a prokaryotic cell. In another embodiment, the prokaryotic cell is an *Escherichia coli* cell. In yet another embodiment, the nucleic acid molecule comprises a nucleic acid sequence at least about 80%, 85%, 90%, 95%, 96%, 97%, 98%, or 99% identical to the nucleic acid sequence of SEQ ID NO: 9.

In an embodiment of the present disclosure, the nucleic acid molecule is codon optimized for expression in a eukaryotic cell. In another embodiment, the eukaryotic cell is a yeast cell or a mammalian cell. In yet another embodiment, the mammalian cell is a human cell.

According to another aspect of the present disclosure, the present disclosure provides a vaccine composition comprising an effective amount of the antigen or the nucleic acid molecule described above.

In an embodiment, the vaccine composition may be used to induce an immune response to RSV in a subject. Thus, in several embodiments, a therapeutically effective amount of a vaccine composition comprising one or more of the antigens of the present disclosure, or a nucleic acid molecule or a plasmid encoding or expressing the antigen, can be administered to a subject to elicit an immune response to RSV.

In another embodiment, a therapeutically effective amount of a vaccine composition comprising one or more of the antigens of the present disclosure, or a nucleic acid molecule or a plasmid encoding or expressing the antigen, is administered to a subject in need under conditions sufficient to prevent or ameliorate an RSV infection in the subject. The vaccine composition is administered in an amount sufficient to elicit an immune response against an RSV antigen, such as RSV F protein, in the subject. In an embodiment of the present disclosure, the vaccine composition of the present disclosure may be administered intranasally or intramuscularly to the subject.

In an embodiment of the present disclosure, the vaccine composition may further comprise a pharmaceutically acceptable carrier and/or an adjuvant.

As used herein, the "pharmaceutically acceptable carrier" includes any and all solvents, dispersion media, antibacterial and antifungal agents, isotonic and absorption delaying agents and the like which may be appropriate for administration of the vaccine composition of the present disclosure. The pharmaceutically acceptable carrier useful for the present disclosure may include, but not limited to, a preservative, a suspending agent, a tackifier, an isotonicity agent, a buffering agent, and a humectant.

In another embodiment of the present disclosure, the adjuvant useful for the present disclosure may include, but not limited to, a CpG oligonucleotide and a hepatitis B core virus-like particle (HBc VLP).

In another embodiment, the vaccine composition administered to the subject comprises a mixture of the antigen and the adjuvant at a weight ratio of 10:1 to 1:10.

In another embodiment of the present disclosure, the vaccine composition promotes a Thl immune response.

Many examples have been used to illustrate the present disclosure. The examples below should not be taken as a limit to the scope of the disclosure.

EXAMPLE

Example 1: Construction of Recombinant RSV Chimera F Protein Expression Vector Full length cDNA sequence of RSV F protein with optimized codon for *Escherichia coli* (*E. coli*) expression was synthesized (Genomics BioSci & Tech). Using this sequence as the PCR template, four gene fragments of RSV F protein were amplified, including nucleotides 457-633 which contain HRN and site Ø (SEQ ID NO: 10), nucleotides 760-849 which contain site II (SEQ ID NO: 11), nucleotides 1264-1314 which contain site IV (SEQ ID NO: 12), and nucleotides 1426-1560 which contain the C-terminal α-helix (HRC) (SEQ ID NO: 13).

These four PCR amplicons were linked by overlapping PCR and connected by a glycine-rich linker, such as GSGS (SEQ ID NO: 38), GGGS (SEQ ID NO: 39), GGSG (SEQ ID NO: 40), SGSG (SEQ ID NO: 41) and GG (SEQ ID NO: 42), to form a constructed gene (named HRØ24), which was then inserted into the NcoI-XhoI restriction sites of pET28b tagged with 6-His at the C-terminus to obtain an HRØ24 plasmid.

The process of construction of HRØ, HRØ-3Ø and HBc plasmids were similar to that of the HRØ24 plasmid, except for the differences as follows.

For the construction of HRØ plasmids, two gene fragments of RSV F protein represented by SEQ ID NOs: 10 and 13 were amplified. These two PCR amplicons were then inserted into the NcoI/BamHI and EcoRI/XhoI restriction sites of pET28a tagged with 6-His at the C-terminus and connected by a glycine-rich linker to obtain an HRØ plasmid.

For the construction of HRØ-3Ø plasmids, two gene fragments of RSV F protein represented by SEQ ID NOs: 10 and 13 were amplified. Further, three site 0 fragments containing NheI/BamHI, BamHI/EcoRI, or EcoRI/HindIII restriction sites were created by PCR. These five PCR amplicons were then inserted into the NcoI/NheI/BamHI/EcoRI/HindIII/XhoI restriction sites of pET28a tagged with 6-His at the C-terminus and connected by a glycine-rich linker to obtain an HRØ-3Ø plasmid.

The resulting plasmids were transformed into *E. coli* BL21 (DE3) competent cells for protein expression. The schematic diagrams of HRØ24, HRØ, and HRØ-3Ø recombinant proteins were shown in FIGS. 1A-1C, respectively.

Example 2: Construction of HBc VLP Expression Vector

Full length cDNA sequence of HBc protein with optimized codon for *Escherichia* co/i (*E. coli*) expression was synthesized (Genomics BioSci & Tech). Using this sequence as the PCR template, nucleotides 1-444 of HBc (SEQ ID NO: 14) was amplified and then inserted into the NcoI-XhoI restriction sites of pET28a tagged with 6-His at the C-terminus. The resulting plasmid was transformed into *E. coli* BL21 (DE3) competent cells for protein expression. The primers used for PCR in Examples 1 and 2 were represented by SEQ ID NOs: 15 to 34, shown in Table 1 below.

TABLE 1

| Primer sequences | |
|---|---|
| Primer | Sequence |
| HRN-NcoI-F | 5'-CCG CCA TGG CCG TGT CTA AGG TGC TGC-3' (SEQ ID NO. 15) |
| HRC-XhoI-R | 5'-CAT GCT CGA GCT TGC CGG CGT TCA CAT TG-3' (SEQ ID NO. 16) |
| HRN-A1-F | 5'-CAT CGT GAA CAA GCA GAG CGG TTC TGG TTC TAA CAG CGA GCT GCT GAG-3' (SEQ ID NO. 17) |
| HRN-A1-R | 5'-CTC AGC AGC TCG CTG TTA GAA CCA GAA CCG CTC TGC TTG TTC ACG ATG-3' (SEQ ID NO. 18) |
| A1-A2-F | 5'-GCA GAT CGT GCG GCA GGG TGG TGG TTC TTG CAC CGC CAG CAA C-3' (SEQ ID NO. 19) |
| A1-A2-R | 5'-GTT GCT GGC GGT GCA AGA ACC ACC ACC CTG CCG CAC GAT CTG C-3' (SEQ ID NO. 20) |
| A2-HRC-F | 5'-AGA CCT TCA GCA ACG GCG GTG GTT CTG GTA ACT TCT ACG ACC CCC TGG-3' (SEQ ID NO. 21) |

TABLE 1-continued

| Primer sequences | |
|---|---|
| Primer | Sequence |
| A2-HRC-R | 5'-CCA GGG GGT CGT AGA AGT TAC CAG AAC CAC CGC CGT TGC TGA AGG TCT-3' (SEQ ID NO. 22) |
| Site Ø-N-F | 5'-GCC GGA TCC AGC AAC ATC AAG GAG AAC AAG TGC AAC GCC GCC AAG AAC TAC ATC GAC AA-3' (SEQ ID NO. 23) |
| Site Ø-C-R | 5'-GCC AAG CTT CTT GTT CAC GAT GGG CAG CAG CTG CTT GTC GAT GTA GTT CTT GGC GGC GTT-3' (SEQ ID NO. 24) |
| HRN-BamHI-R | 5'-GCC GGA TCC AGA ACC AGA ACC GCT CTG CTT G-3' (SEQ ID NO. 25) |
| HRC-EcoRI-F | 5'-CGG AAT TCG GTG GTT CTG GTA ACT TCT ACG AC-3' (SEQ ID NO. 26) |
| Site Ø-NheI-F | 5'-CTA GCT AGC AGC AAC ATC AAG GAG AAC-3' (SEQ ID NO. 27) |
| Site Ø-BamHI-R | 5'-GCC GGA TCC GCC TCC CTT GTT CAC GAT GGG CAG C-3' (SEQ ID NO. 28) |
| Site Ø-BamHI-F | 5'-GCC GGA TCC AGC AAC ATC AAG GAG AAC-3' (SEQ ID NO. 29) |
| Site Ø-EcoRI-R | 5'-CGG AAT TCG CCT CCC TTG TTC ACG ATG GGC AGC-3' (SEQ ID NO. 30) |
| Site Ø-EcoRI-F | 5'-CGG AAT TCA GCA ACA TCA AGG AGA AC-3' (SEQ ID NO. 31) |
| Site Ø-HindIII-R | 5'-CCC AAG CTT CTT GTT CAC GAT GGG CAG C-3' (SEQ ID NO. 32) |
| HBc148-NcoI-F | 5'-CCG CCA TGG ACA TTG ACC CTT ATA AAG-3' (SEQ ID NO. 33) |
| HBc148-XhoI-R | 5'-CAT GCT CGA GAA CAG TAG TTT CCG GAA GTG-3' (SEQ ID NO. 34) |

Example 3: Recombinant Protein Expression and Purification

The recombinant RSV F protein-6-His and HBc-6-His were expressed in the transformed *E. coli* BL21 (DE3) obtained from Examples 1 and 2, and purified using nickel affinity chromatography, respectively. Eluted (with 500 mM imidazole, 50 mM $NaH_2PO_4$, 300 mM NaCl, pH 8.0) protein was buffer exchanged by gradient dialyzing 1 volume of sample against 200 volumes of dialyzing buffer (from 350 mM, 150 mM to 0 mM imidazole in 1×PBS) for 12 h in each step. The dialyzed protein-6-His was concentrated using a centrifugal concentrator (10,000 MWCO, Sartorius) to reach a concentration about 1 mg/mL. Molecule size and purity of the protein were determined by SDS-PAGE.

Figure 2A:
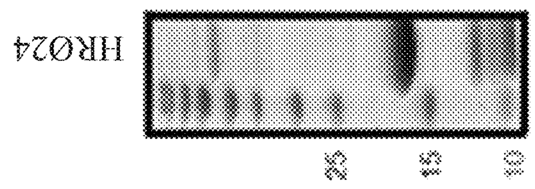
FIGS. 2A-2I are results of SDS-PAGE analysis of HRØ24, HRØ, HRØ-3Ø recombinant proteins, and HBc.
Figure 2B:
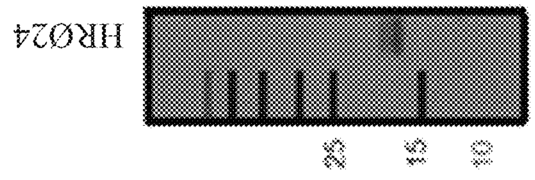
Figure 2C:
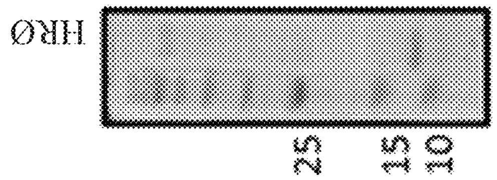
Figure 2D:
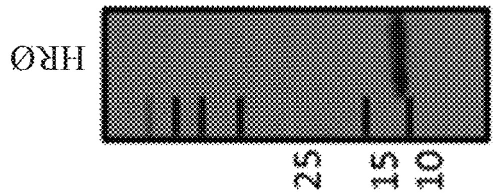
Figure 2E:
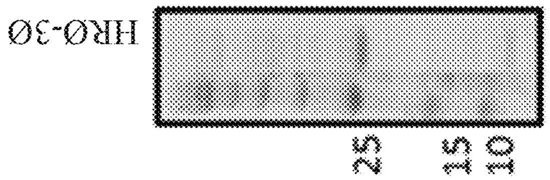
Figure 2F:
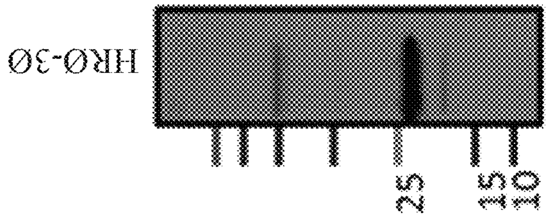
Figure 2G:
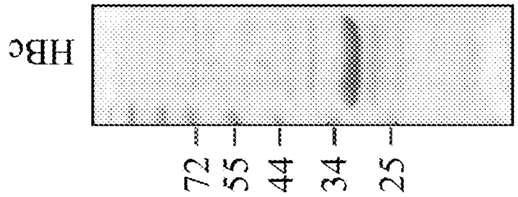
Figure 2H:
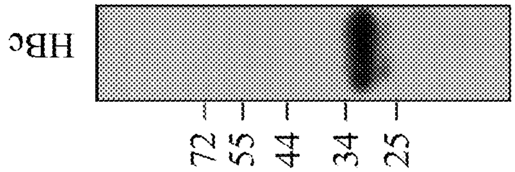
Figure 2I:
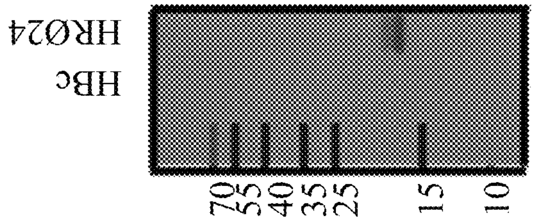

A band of identical mobility was detected by immunoblotting using antibodies directed against His tag, and the results were shown in FIGS. 2B, 2D, and 2F. A band of identical mobility was detected by immunoblotting using antibodies directed against HBc and RSV, and the results were shown in FIGS. 2H and 21, respectively. Densitometric scanning of Coomassie blue stained gels revealed that the purified proteins HRØ24, HRØ, HRØ-3Ø and HBc amounted to more than 90% of the total protein (FIGS. 2A, 2C, 2E, and 2G), which was sufficiently pure for immunizations.

Example 4: Transmission Electron Microscope (TEM) Images of HRØ24 and HBc Recombinant Proteins 8 μg of purified HBc VLPs in PBS were adsorbed onto a copper grid (300 mesh) for 3 min at room temperature. Then, the grids were dried gently using filter paper. After staining with 1% uranyl acetate aqueous solution for 30 seconds (s), the excess liquid was removed. The grids were examined with JEM-1400 electron microscope at 80 kV.

Figure 3A:
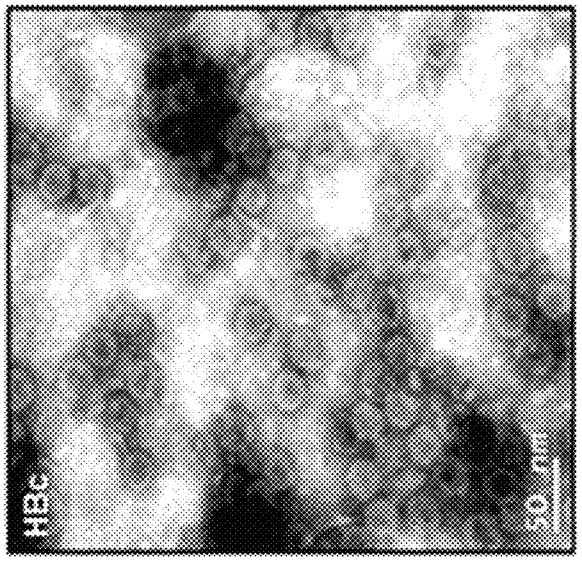
FIGS. 3A and 3B show the transmission electron microscope (TEM) images of purified HBc and HRØ24 recombinant proteins, respectively.
Figure 3B:
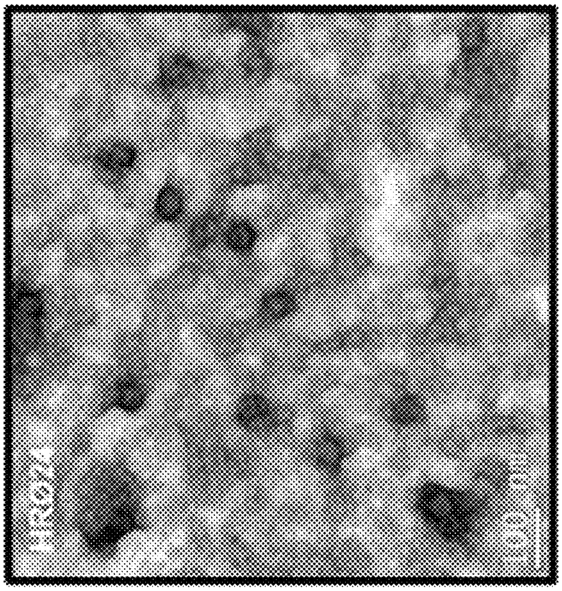

The HBc VLPs have been confirmed to form virus-like particles by TEM (FIG. 3A). The TEM image also showed that the recombinant HRØ24 protein formed about 50 nm polymerized nanoparticles (FIG. 3B).

Example 5: Animal Immunization

1. Preparation of RSV A2 Strain Stock

RSV A2 strain was obtained from ATCC. Propagation of the virus was performed in HEp-2 cells ATCC. Cells grown in 100 mm Petri dish (Thermo Scientific) up to 80% confluency were inoculated with RSV A2 at an m.o.i. (multiplicity of infection) of 0.2. Virus adsorption was carried out in serum free Dulbecco's Modified Eagle's medium (DMEM) in a $CO_2$ incubator at 37° C. After 2 hours, medium was replaced with DMEM supplemented with 2% fetal bovine serum, and the dishes were incubated for another 48 to 72 hours. Supernatants which contain the virus were separated from cell debris by centrifugation at 3,000 rpm for 10 min. Virus was then concentrated by a centrifugal concentrator (100,000 MWCO, Sartorius).

2. RSV Plaque Assay

RSV virus titer was determined by plaque assay. Confluent monolayer of HEp-2 cells in 12-well plates were washed with 1×PB S and then infected with RSV A2 virus at various dilutions ($10^{-3}$ to $10^{-7}$). After 2 hours of virus adsorption, supernatant was removed, and the cell monolayer was washed with 1×PBS, followed by overlaying with DMEM+2% fetal bovine serum+0.3% agarose. After 5 days incubation at 37° C. in a $CO_2$ incubator, cells were fixed with 10% formalin and stained with 0.05% crystal violet for plaque quantification.

3. Vaccine Administration and RSV Challenge

Figure 4:
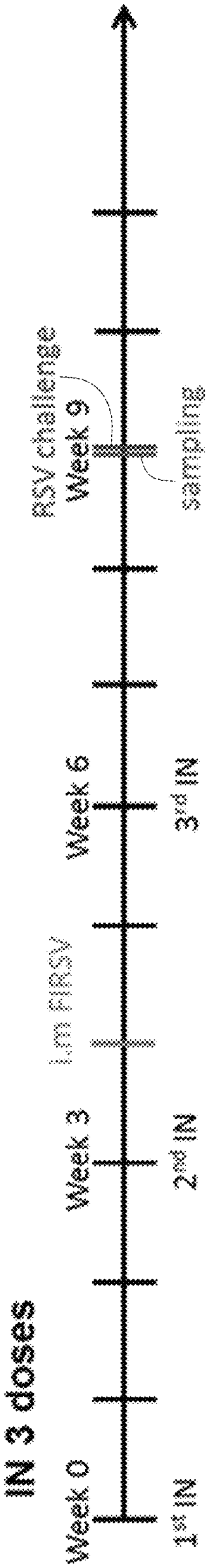
FIG. 4 shows the intranasal (IN) immunization schedule. Groups of mice are immunized 3 times with vaccine candidates on week 0, 3, and 6, and received RSV challenge on week 9. A group immunized with formalin-fixed RSV (FIRSV) intramuscularly (i.m) on week 4 before RSV challenge is also included. Mouse serum and bronchoalveolar lavage fluid (BALF) are collected from separate groups with identical dosing regimen 2 days before RSV challenge.
Figure 5B:
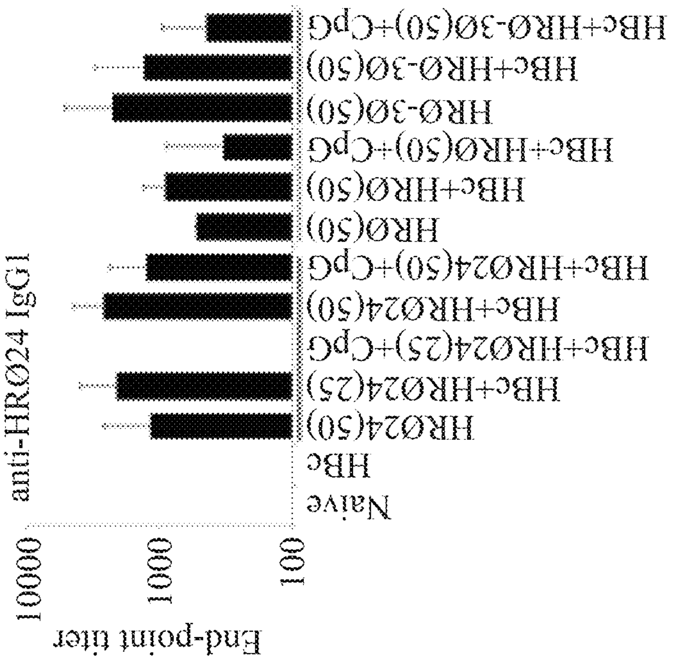
FIGS. 5A-5E show HRØ24-specific antibody responses in mice received 3 doses of intranasal administration of HRØ24, HRØ, or HRØ-3Ø mixed with or without HBc or CpG. Serum and BALF are collected from the mice 2 days before RSV challenge.
Figure 5A:
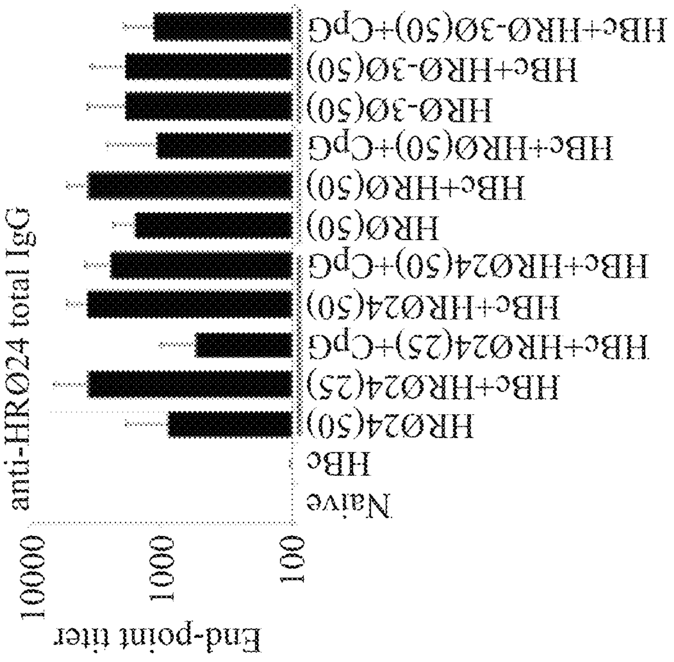
Figure 5D:
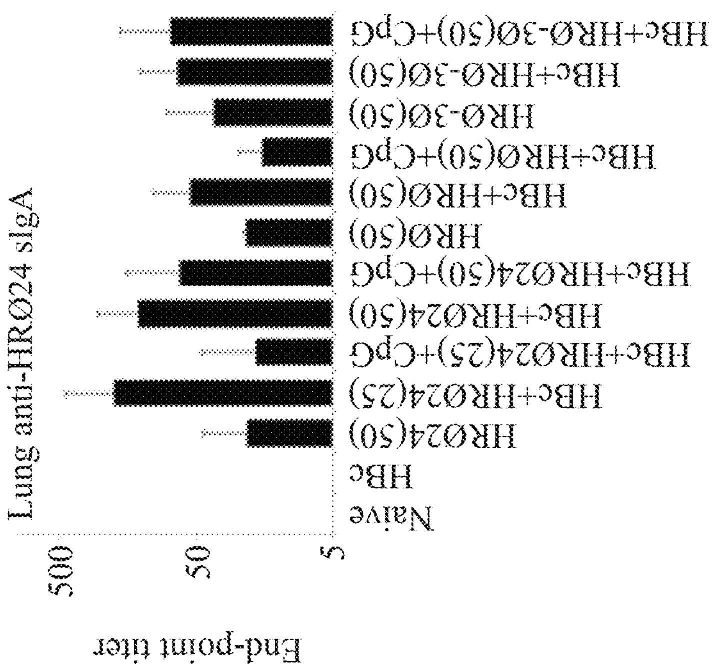
Figure 5C:
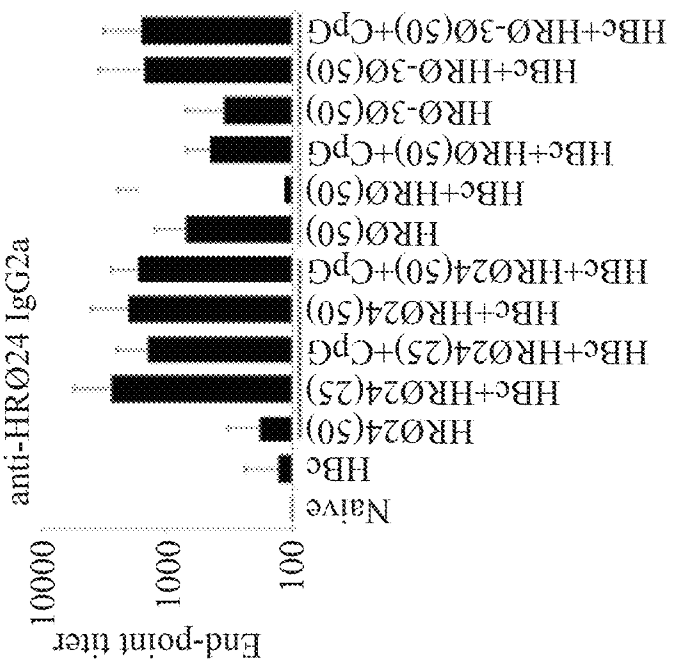
Figure 5E:
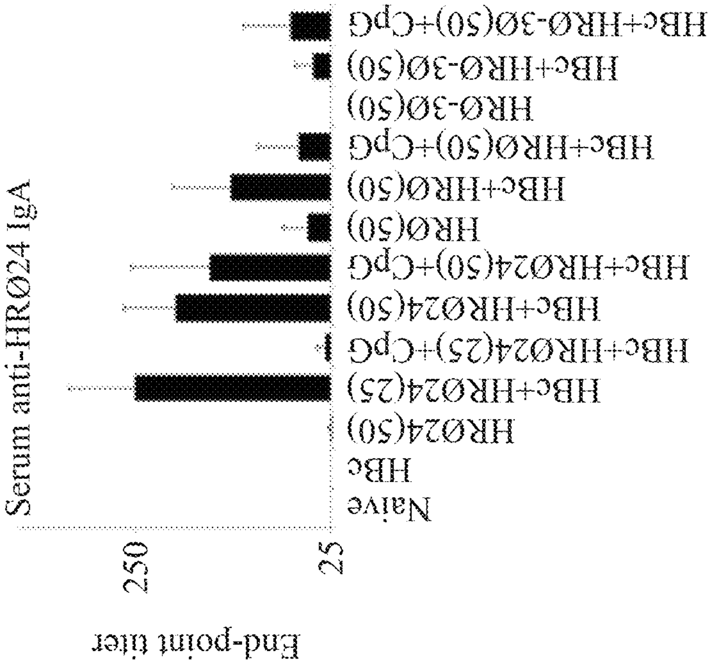

Pathogen-free C57BL/6J female mice (6-8 weeks old) were randomly divided into several groups and immunized by the intranasal (i.n) route with vaccine candidates on day 0, 21, and 42 and challenged with $1\times10^6$ p.f.u. RSV on day 63 (FIG. 4). The vaccine candidates include: 50 μg HRØ24; 25 μg HBc VLPs+25 μg HRØ24; 25 μg HBc VLPs+25 μg HRØ24+20 μg CpG (TCGTCGTTTTCGGCGCGCGCCG, SEQ ID NO. 37) (Genomics, Taiwan) 25 μg HBc VLPs+50 μg HRØ24; 25 μg HBc VLPs+50 g HRØ24+20 μg CpG; 50 μg HRØ; 25 μg HBc VLPs+50 μg HRØ; 25 μg HBc VLPs+50 g HRØ+20 μg CpG; 50 μg HRØ-30; 25 μg HBc VLPs+50 μg HRØ-30; and 25 μg HBc VLPs+50 ag HRØ-30+20 μg CpG. A naive control group and a group immunized with 25 μg HBc VLPs intranasally on day 0, 21, and 42 were included. A group immunized with $1\times10^5$ p.f.u. FIRSV intramuscularly (i.m) on day 35 was also included.

Before RSV challenge, mouse serum and bronchoalveolar lavage fluid (BALF) were collected from separate groups with identical dosing regimen on day 61. For RSV challenge, the mice were anesthetized with 1.5% isoflurane and then infected by intranasal inoculation of $1\times10^6$ p.f.u. RSV on day 63. After RSV challenge, body weights of the mice were monitored for 5 days. Finally, the mice were sacrificed on day 68, and the individual lungs were collected for virus load and histopathology experiments.

Example 6: Evaluation of Antibody Response Elicited by Vaccine Candidates

Serum and BALF collected from the immunized mice as described in Example 5 were tested for antibody responses by enzyme-linked immunosorbent assay (ELISA). Briefly, a 96-well plate was coated with 50 μL of purified HRØ24 (10 μg/ml) overnight at 4° C. The plate was blocked with 2% BSA for 1 hour at 37° C., and incubated with serial dilutions of serum samples ($10^{-2}$ to $5.12\times10^{-4}$) or BALF ($10^{-1}$ to $1.28\times10^{-3}$) in assay diluent (1% BSA, 0.05% Tween 20 in 1×PBS) for 2 hours at room temperature. Dilution curve was drawn for each sample, and endpoint titers were calculated as the reciprocal of the dilution producing an optical density that was 0.1 U greater than the background value (1/50 dilution of a pooled pre-immune serum or 1/5 dilution of a pooled naive BALF). IgG titers lower than 50 (negative samples) or secretory IgA (sIgA) titers lower than 5 were arbitrarily assigned as 50 or 5.

Referring to FIGS. 5A-5E, it is shown that dosing with HRØ24, HRØ and HRØ-3Ø can elicit serum HRØ24-specific total IgG, IgG1, IgG2a, and lung HRØ24-specific sIgA. Furthermore, by using HBc as an adjuvant, HRØ24, HRØ and HRØ-3Ø can elicit significant higher serum HRØ24-specific total IgG, IgG1, IgG2a, IgA and lung HRØ24-specific sIgA, in which the highest end-point titers were observed in the HBc/HRØ24 group. Moreover, by using the mixture of HBc and CpG as an adjuvant, HRØ24 can also elicit higher serum HRØ24-specific total IgG, IgG1, IgG2a, IgA and lung HRØ24-specific sIgA.

Example 7: Effects of Vaccine Candidates on Protecting Mice Against RSV Infection To evaluate the efficacy when dosing the vaccine candidates 3 times, the immunized mice challenged with live RSV A2 strain as described in Example 5 were used.

1. Mice Body Weight Changes after RSV Challenge

Figure 6B:
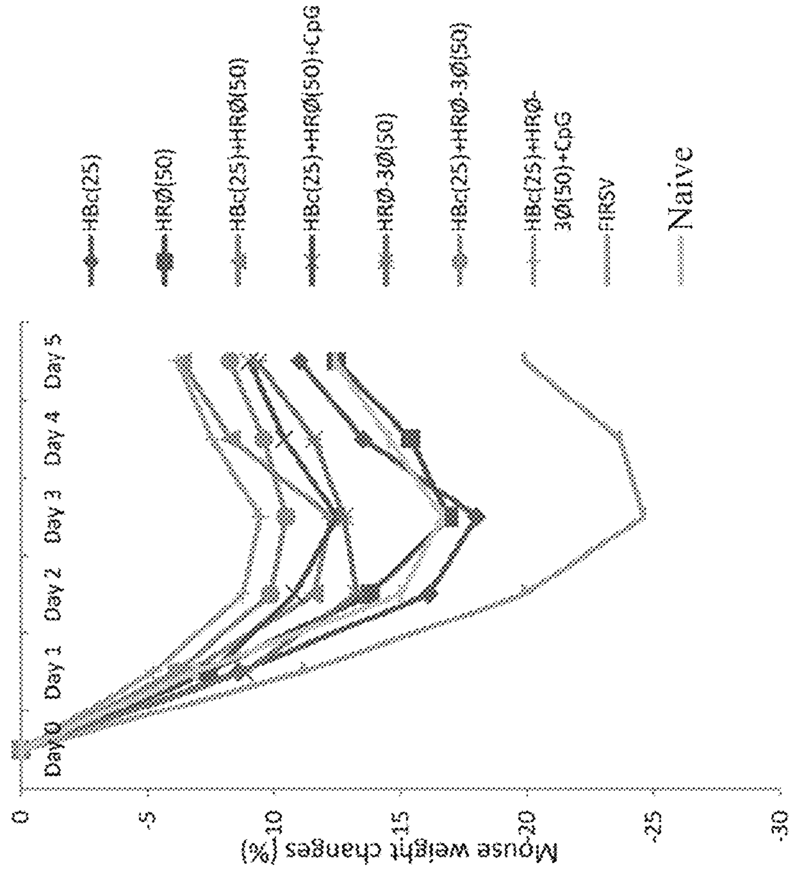
FIGS. 6A and 6B show mouse body weight changes after RSV challenge. The body weight of naive or vaccinated mice is monitored for 5 days after RSV challenge. Body weight changes are presented as the weight loss percentage compared to day 0.
Figure 6A:
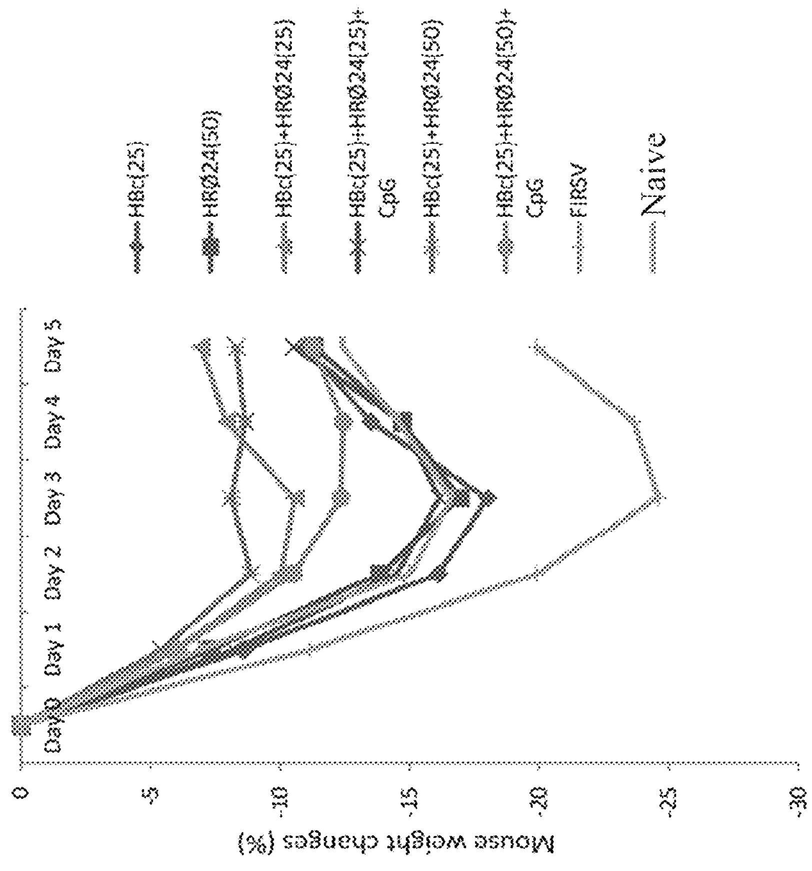

Body weight change of mice following challenge infection is the most important indicator to assess vaccine protective efficacy. Referring to FIGS. 6A and 6B, mice immunized with HRØ24/HBc, HRØ24/HBc/CpG, HRØ-30, HRØ-30/HBc, HRØ-30/HBc/CpG, HRØ/HBc or HRØ/HBc/CpG showed less body weight loss compared with the naive group after day 2 post challenge. More specifically, FIG. 6A showed about 8-11% body weight loss in the groups of mice received HRØ24 mixed with HBc. Also, mice immunized with 25 μg and 50 μg HRØ24 mixed with HBc/CpG showed about 16% and 12% body weight loss, respectively, at day 3 post challenge. In addition, FIG. 6B demonstrated that mice immunized with HRØ/HBc or HRØ-3Ø/HBc mixture showed about 12% or 10% body weight loss at day 3 post challenge. In contrast, mice received FIRSV intramuscularly showed the highest body weight loss every day and showed about 25% body weight loss at day 3 post challenge.

Therefore, the present disclosure provides a better protection to prevent mouse weight loss and an accelerated recovery from initial body weight loss following live RSV challenge. These are evidence that anti-viral immunity elicited by the antigen of the present disclosure confer protection against live RSV A2 strain virus.

2. Lung Histopathology after RSV Challenge

For histological analysis, lung samples were fixed in 10% neutral buffered formalin for 24 hrs, embedded in paraffin blocks, sectioned into a thickness of 5 m, and stained with hematoxylin and eosin (H&E).

Figure 7:
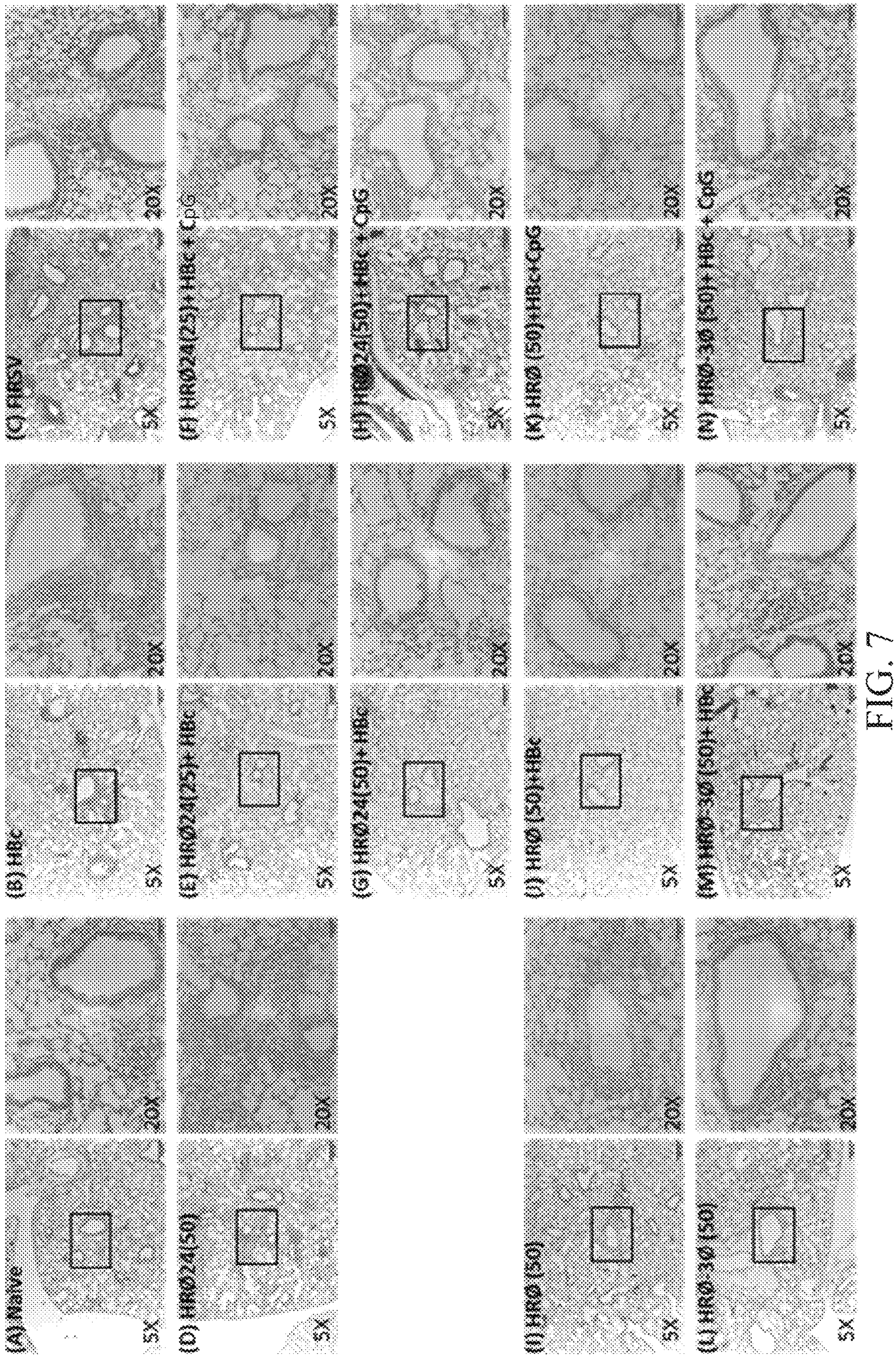
FIG. 7 shows lung histopathology. Lung tissues are collected from naive or vaccinated mice at day 5 post RSV challenge for histology analysis.

Referring to FIG. 7, lung histopathological changes were observed in the naive group or mice immunized with HBc, HRØ24, HRØ, HRØ-3Ø or FIRSV, wherein FIRSV immunized mice showed a severe level of histopathology. In contrast, mice received HRØ24/HBc, HRØ/HBc or HRØ-30/HBc mixture showed none to moderate level of histopathology upon RSV challenge.

3. Lung Virus Load by Quantitative RT-PCR (qRT-PCR)

Control of lung viral loads is an important parameter in assessing vaccine efficacy since there would be a positive correlation between viral replication and clinical disease during natural or experimental infections (DeVincenzo, J. P., et al., 2005; Karron, R. A., et al., 1997). Therefore, qRT-PCR targeting RSV N gene was performed to quantify mRNA levels in lung tissues.

Lung extracts were prepared as homogenates using frosted glass slides. Total RNA was prepared by Qiagen RNeasy kit from homogenated samples. Two steps qRT-PCR was performed. The first-strand cDNA was amplified from 2 μg total RNA by SuperScript III Reverse Transcriptase (Invitrogen). The following primer pair was used for qRT-PCR: RSV-A-N-F730: GCAGGATTGTTTATGAATGCC (SEQ ID NO: 35) and RSV-A-N-R857: TCCACAACTTGTTCCATTTC (SEQ ID NO: 36) for RSV subgroup A viruses. Following optimization, reactions contained: each primer at 200 nM, 1×Power SYBR Green PCR Master Mix (ABI), 1 μL of cDNA, and water to 10 μL. Real-time PCR was performed using the ABI instrument with the following conditions: 95° C. for 10 min (1×), 95° C. for 15 sec, 60° C. for 60 sec (40×). DNA standards were used to verify the performance of each PCR run and to facilitate the quantification of experimental samples.

Figure 8:
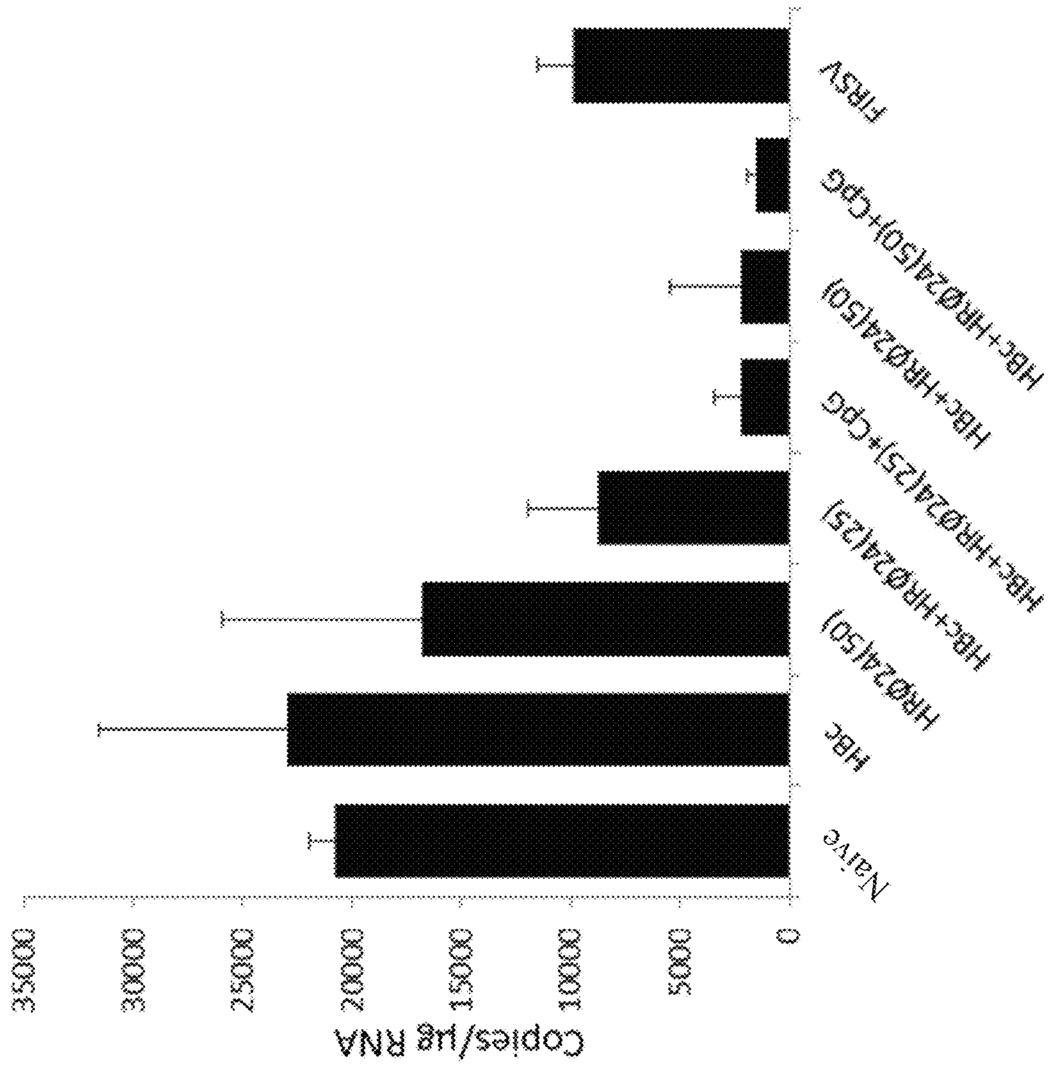
FIG. 8 shows lung virus load. Lung tissues are collected from naive or vaccinated mice at day 5 post challenge for lung virus load analysis by qRT-PCR targeting RSV N gene.

Referring to FIG. 8, lower levels of virus titers were observed in the lungs of mice immunized with HRØ24, HRØ24/HBc, HRØ24/HBc/CpG or FIRSV compared with the naive group. The lung viral titers were significantly lower in the HRØ24/HBc/CpG or HRØ24(50)/HBc groups compared to those in the FIRSV group. The results showed that significantly lower viral load was recovered from lungs of animals immunized intranasally with the HRØ24/HBc mixture and the HRØ24/HBc/CpG mixture.

Therefore, these results demonstrated that the antigen of the present disclosure can induce both systemic and mucosal antibody responses specific for RSV. Mice immunized with the antigen of the present disclosure showed protection against RSV without causing lung disease. The antigen of the present disclosure did not over-stimulate lymphocytes compared to FIRSV in a mouse model and offer as a potential safe RSV vaccine candidate.

Also, the sequence of the antigen of the present disclosure is relatively shorter than the wild type RSV F protein and is therefore relatively easy in mass production. Moreover, the antigen of the present disclosure retains only critical antigenic sites and is therefore more helpful in increasing the specificity of antibody identification and avoiding unnecessary reactions such as allergy than wild-type RSV F proteins.

The present disclosure has been described using exemplary embodiments in detail in the above. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

What is claimed is:

1. An antigen comprising a recombinant respiratory syncytial virus (RSV) F protein, wherein the recombinant RSV F protein comprises an antigenic region flanked with an N-terminal heptad repeat (HRN) region and a C-terminal heptad repeat (HRC) region, and wherein the HRN region and the HRC region comprise amino acid sequences of SEQ ID NO: 1 and SEQ ID NO: 2, respectively;

the antigenic region comprises two or more antigenic sites selected from the group consisting of site Ø, site II, and site IV including amino acid sequences of SEQ ID NO: 3, SEQ ID NO: 4, and SEQ ID NO: 5, respectively; and the antigenic sites are linked to each other by a linker independently consisting of 2 to 20 amino acids.

2. The antigen of claim 1, wherein the antigenic region comprises site II and site IV.

3. The antigen of claim 2, wherein the HRC region is linked to the site IV by the linker.

4. The antigen of claim 3, wherein the recombinant RSV F protein comprises an amino acid sequence of SEQ ID NO: 8.

5. The antigen of claim 1, wherein the antigenic region comprises three site Ø.

6. The antigen of claim 5, wherein the recombinant RSV F protein comprises an amino acid sequence of SEQ ID NO: 7.

7. The antigen of claim 1, wherein the linker comprises an amino acid sequence of any one of SEQ ID NO: 38, SEQ ID NO: 39, SEQ ID NO: 40, SEQ ID NO: 41, and SEQ ID NO: 42.

8. The antigen of claim 1, wherein the antigen specifically binds to a 5C4, a D25, or an AM22 prefusion-specific antibody.

9. A nucleic acid molecule encoding the antigen of claim 1.

10. The nucleic acid molecule of claim 9, wherein the nucleic acid molecule is codon optimized for expression in a prokaryotic cell.

11. The nucleic acid molecule of claim 10, wherein the prokaryotic cell is an *Escherichia coli* cell.

12. The nucleic acid molecule of claim 11, wherein the nucleic acid molecule comprises a nucleic acid sequence at least 80% identical to a nucleic acid sequence of SEQ ID No: 9.

13. The nucleic acid molecule of claim 9, wherein the nucleic acid molecule is codon optimized for expression in a eukaryotic cell.

14. The nucleic acid molecule of claim 13, wherein the eukaryotic cell is a yeast cell or a mammalian cell.

15. The nucleic acid molecule of claim 14, wherein the mammalian cell is a human cell.

16. A vaccine composition comprising an effective amount of the antigen of claim 1.

17. The vaccine composition of claim 16, further comprising a pharmaceutically acceptable carrier and/or an adjuvant.

18. The vaccine composition of claim 17, wherein the adjuvant is a CpG oligonucleotide or a hepatitis B core virus-like particle.

19. The vaccine composition of claim 18, wherein the vaccine composition promotes a Thl immune response.

* * * * *

SEQUENCE LISTING

<160> NUMBER OF SEQ ID NOS: 37

<210> SEQ ID NO 1
<211> LENGTH: 60
<212> TYPE: PRT
<213> ORGANISM: respiratory syncytial virus

<400> SEQUENCE: 1

Met Ala Val Ser Lys Val Leu His Leu Glu Gly Glu Val Asn Lys Ile
1 5 10 15

Lys Ser Ala Leu Leu Ser Thr Asn Lys Ala Val Val Ser Leu Ser Asn
20 25 30

Gly Val Ser Val Leu Thr Ser Lys Val Leu Asp Leu Lys Asn Tyr Ile
35 40 45

Asp Lys Gln Leu Leu Pro Ile Val Asn Lys Gln Ser
50 55 60

<210> SEQ ID NO 2
<211> LENGTH: 45
<212> TYPE: PRT
<213> ORGANISM: respiratory syncytial virus

<400> SEQUENCE: 2

Asn Phe Tyr Asp Pro Leu Val Phe Pro Ser Asp Glu Phe Asp Ala Ser
1 5 10 15

Ile Ser Gln Val Asn Glu Lys Ile Asn Gln Ser Leu Ala Phe Ile Arg
20 25 30

Lys Ser Asp Glu Leu Leu His Asn Val Asn Ala Gly Lys
35 40 45

<210> SEQ ID NO 3
<211> LENGTH: 14
<212> TYPE: PRT
<213> ORGANISM: respiratory syncytial virus -continued

<400> SEQUENCE: 3

```
Lys Asn Tyr Ile Asp Lys Gln Leu Leu Pro Ile Val Asn Lys
1               5                   10
```

<210> SEQ ID NO 4
<211> LENGTH: 23
<212> TYPE: PRT
<213> ORGANISM: respiratory syncytial virus

<400> SEQUENCE: 4

```
Asn Ser Glu Leu Leu Ser Leu Ile Asn Asp Met Pro Ile Thr Asn Asp
1               5                   10                  15

Gln Lys Lys Leu Met Ser Asn
            20
```

<210> SEQ ID NO 5
<211> LENGTH: 10
<212> TYPE: PRT
<213> ORGANISM: respiratory syncytial virus

<400> SEQUENCE: 5

```
Lys Asn Arg Gly Ile Ile Lys Thr Phe Ser
1               5                   10
```

<210> SEQ ID NO 6
<211> LENGTH: 119
<212> TYPE: PRT
<213> ORGANISM: Artificial Sequence
<220> FEATURE:
<223> OTHER INFORMATION: recombinant RSV F protein HRO

<400> SEQUENCE: 6

```
Met Ala Val Ser Lys Val Leu His Leu Glu Gly Glu Val Asn Lys Ile
1               5                   10                  15

Lys Ser Ala Leu Leu Ser Thr Asn Lys Ala Val Val Ser Leu Ser Asn
            20                  25                  30

Gly Val Ser Val Leu Thr Ser Lys Val Leu Asp Leu Lys Asn Tyr Ile
        35                  40                  45

Asp Lys Gln Leu Leu Pro Ile Val Asn Lys Gln Ser Gly Ser Gly Ser
    50                  55                  60

Gly Ser Glu Phe Gly Gly Ser Gly Asn Phe Tyr Asp Pro Leu Val Phe
65                  70                  75                  80

Pro Ser Asp Glu Phe Asp Ala Ser Ile Ser Gln Val Asn Glu Lys Ile
                85                  90                  95

Asn Gln Ser Leu Ala Phe Ile Arg Lys Ser Asp Glu Leu Leu His Asn
            100                 105                 110

Val Asn Ala Gly Lys Leu Glu
        115
```

<210> SEQ ID NO 7
<211> LENGTH: 202
<212> TYPE: PRT
<213> ORGANISM: Artificial Sequence
<220> FEATURE:
<223> OTHER INFORMATION: recombinant RSV F protein HRO-30

<400> SEQUENCE: 7

```
Met Ala Val Ser Lys Val Leu His Leu Glu Gly Glu Val Asn Lys Ile
1               5                   10                  15

Lys Ser Ala Leu Leu Ser Thr Asn Lys Ala Val Val Ser Leu Ser Asn
            20                  25                  30
```

-continued

```
Gly Val Ser Val Leu Thr Ser Lys Val Leu Asp Leu Lys Asn Tyr Ile
        35                  40                  45

Asp Lys Gln Leu Leu Pro Ile Val Asn Lys Gln Ser Gly Ser Gly Ser
    50                  55                  60

Ala Ser Ser Asn Ile Lys Glu Asn Lys Cys Asn Ala Ala Lys Asn Tyr
65                  70                  75                  80

Ile Asp Lys Gln Leu Leu Pro Ile Val Asn Lys Gly Gly Gly Ser Ser
                85                  90                  95

Asn Ile Lys Glu Asn Lys Cys Asn Ala Ala Lys Asn Tyr Ile Asp Lys
            100                 105                 110

Gln Leu Leu Pro Ile Val Asn Lys Gly Gly Glu Phe Ser Asn Ile Lys
        115                 120                 125

Glu Asn Lys Cys Asn Ala Ala Lys Asn Tyr Ile Asp Lys Gln Leu Leu
    130                 135                 140

Pro Ile Val Asn Lys Lys Leu Gly Gly Ser Gly Asn Phe Tyr Asp Pro
145                 150                 155                 160

Leu Val Phe Pro Ser Asp Glu Phe Asp Ala Ser Ile Ser Gln Val Asn
                165                 170                 175

Glu Lys Ile Asn Gln Ser Leu Ala Phe Ile Arg Lys Ser Asp Glu Leu
            180                 185                 190

Leu His Asn Val Asn Ala Gly Lys Leu Glu
        195                 200


<210> SEQ ID NO 8
<211> LENGTH: 164
<212> TYPE: PRT
<213> ORGANISM: Artificial Sequence
<220> FEATURE:
<223> OTHER INFORMATION: recombinant RSV F protein HRO24

<400> SEQUENCE: 8

Met Ala Val Ser Lys Val Leu His Leu Glu Gly Glu Val Asn Lys Ile
1               5                   10                  15

Lys Ser Ala Leu Leu Ser Thr Asn Lys Ala Val Val Ser Leu Ser Asn
            20                  25                  30

Gly Val Ser Val Leu Thr Ser Lys Val Leu Asp Leu Lys Asn Tyr Ile
        35                  40                  45

Asp Lys Gln Leu Leu Pro Ile Val Asn Lys Gln Ser Gly Ser Gly Ser
    50                  55                  60

Asn Ser Glu Leu Leu Ser Leu Ile Asn Asp Met Pro Ile Thr Asn Asp
65                  70                  75                  80

Gln Lys Lys Leu Met Ser Asn Asn Val Gln Ile Val Arg Gln Gly Gly
                85                  90                  95

Gly Ser Cys Thr Ala Ser Asn Lys Asn Arg Gly Ile Ile Lys Thr Phe
            100                 105                 110

Ser Asn Gly Gly Gly Ser Gly Asn Phe Tyr Asp Pro Leu Val Phe Pro
        115                 120                 125

Ser Asp Glu Phe Asp Ala Ser Ile Ser Gln Val Asn Glu Lys Ile Asn
    130                 135                 140

Gln Ser Leu Ala Phe Ile Arg Lys Ser Asp Glu Leu Leu His Asn Val
145                 150                 155                 160

Asn Ala Gly Lys
```

-continued

<210> SEQ ID NO 9
<211> LENGTH: 492
<212> TYPE: DNA
<213> ORGANISM: Artificial Sequence
<220> FEATURE:
<223> OTHER INFORMATION: recombinant RSV F protein

<400> SEQUENCE: 9

```
atggccgtgt ctaaggtgct gcacctggag ggagaggtga acaagatcaa gagcgccctg     60

ctgagcacca ataaggccgt ggtgagcctg agcaatggcg tgagcgtgct gacaagcaag    120

gtgctggacc tcaagaacta catcgacaag cagctgctgc ccatcgtgaa caagcagagc    180

ggttctggtt ctaacagcga gctgctgagc ctgatcaacg acatgcccat caccaacgac    240

cagaagaagc tgatgtccaa caacgtgcag atcgtgcggc agggtggtgg ttcttgcacc    300

gccagcaaca agaaccgcgg catcatcaag accttcagca acggcggtgg ttctggtaac    360

ttctacgacc ccctggtgtt ccctagcgac gagttcgatg ccagcatcag ccaggtgaac    420

gagaagatca accagagcct ggccttcatc aggaagagcg acgagctgct gcacaatgtg    480

aacgccggca ag                                                        492
```

<210> SEQ ID NO 10
<211> LENGTH: 177
<212> TYPE: DNA
<213> ORGANISM: respiratory syncytial virus

<400> SEQUENCE: 10

```
gccgtgtcta aggtgctgca cctggaggga gaggtgaaca agatcaagag cgccctgctg     60

agcaccaata aggccgtggt gagcctgagc aatggcgtga gcgtgctgac aagcaaggtg    120

ctggacctca agaactacat cgacaagcag ctgctgccca tcgtgaacaa gcagagc       177
```

<210> SEQ ID NO 11
<211> LENGTH: 90
<212> TYPE: DNA
<213> ORGANISM: respiratory syncytial virus

<400> SEQUENCE: 11

```
aacagcgagc tgctgagcct gatcaacgac atgcccatca ccaacgacca gaagaagctg     60

atgtccaaca acgtgcagat cgtgcggcag                                      90
```

<210> SEQ ID NO 12
<211> LENGTH: 51
<212> TYPE: DNA
<213> ORGANISM: respiratory syncytial virus

<400> SEQUENCE: 12

```
tgcaccgcca gcaacaagaa ccgcggcatc atcaagacct tcagcaacgg c              51
```

<210> SEQ ID NO 13
<211> LENGTH: 135
<212> TYPE: DNA
<213> ORGANISM: respiratory syncytial virus

<400> SEQUENCE: 13

```
aacttctacg acccccctggt gttccctagc gacgagttcg atgccagcat cagccaggtg     60

aacgagaaga tcaaccagag cctggccttc atcaggaaga gcgacgagct gctgcacaat    120

gtgaacgccg gcaag                                                     135
```

-continued

<210> SEQ ID NO 14
<211> LENGTH: 462
<212> TYPE: DNA
<213> ORGANISM: Hepatitis B virus

<400> SEQUENCE: 14
atggacattg acccttataa agaatttgga gctactgtgg agttactctc gtttttgcct 60
tctgacttct ttccttccgt cagagatctt ctagacaccg cctcagctct gtatcgagaa 120
gccttagagt ctcctgagca ttgctcacct caccatactg cactcaggca agccattctc 180
tgctgggggg aattgatgac tctagctacc tgggtgggta ataatttgga agatccagca 240
tccagggatc tagtagtcaa ttatgttaat actaacatgg gtttaaagat caggcaacta 300
ttgtggtttc atatatcttg ccttactttt ggaagagaga ctgtacttga atatttggtc 360
tctttcggag tgtggattcg cactcctcca gcctatagac caccaaatgc ccctatctta 420
tcaacacttc cggaaactac tgttcaccac caccaccacc ac 462

<210> SEQ ID NO 15
<211> LENGTH: 27
<212> TYPE: DNA
<213> ORGANISM: Artificial Sequence
<220> FEATURE:
<223> OTHER INFORMATION: HRN-NcoI-F
<220> FEATURE:
<221> NAME/KEY: primer_bind
<222> LOCATION: (1)..(27)

<400> SEQUENCE: 15
ccgccatggc cgtgtctaag gtgctgc 27

<210> SEQ ID NO 16
<211> LENGTH: 29
<212> TYPE: DNA
<213> ORGANISM: Artificial Sequence
<220> FEATURE:
<223> OTHER INFORMATION: HRC-XhoI-R
<220> FEATURE:
<221> NAME/KEY: primer_bind
<222> LOCATION: (1)..(29)

<400> SEQUENCE: 16
catgctcgag cttgccggcg ttcacattg 29

<210> SEQ ID NO 17
<211> LENGTH: 48
<212> TYPE: DNA
<213> ORGANISM: Artificial Sequence
<220> FEATURE:
<223> OTHER INFORMATION: HRN-A1-F
<220> FEATURE:
<221> NAME/KEY: primer_bind
<222> LOCATION: (1)..(48)

<400> SEQUENCE: 17
catcgtgaac aagcagagcg gttctggttc taacagcgag ctgctgag 48

<210> SEQ ID NO 18
<211> LENGTH: 48
<212> TYPE: DNA
<213> ORGANISM: Artificial Sequence
<220> FEATURE:
<223> OTHER INFORMATION: HRN-A1-R
<220> FEATURE:
<221> NAME/KEY: primer_bind
<222> LOCATION: (1)..(48)

<400> SEQUENCE: 18
ctcagcagct cgctgttaga accagaaccg ctctgcttgt tcacgatg 48

<210> SEQ ID NO 19
<211> LENGTH: 43
<212> TYPE: DNA
<213> ORGANISM: Artificial Sequence
<220> FEATURE:
<223> OTHER INFORMATION: A1-A2-F
<220> FEATURE:
<221> NAME/KEY: primer_bind
<222> LOCATION: (1)..(43)

<400> SEQUENCE: 19
gcagatcgtg cggcagggtg gtggttcttg caccgccagc aac 43

<210> SEQ ID NO 20
<211> LENGTH: 43
<212> TYPE: DNA
<213> ORGANISM: Artificial Sequence
<220> FEATURE:
<223> OTHER INFORMATION: A1-A2-R
<220> FEATURE:
<221> NAME/KEY: primer_bind
<222> LOCATION: (1)..(43)

<400> SEQUENCE: 20
gttgctggcg gtgcaagaac caccaccctg ccgcacgatc tgc 43

<210> SEQ ID NO 21
<211> LENGTH: 48
<212> TYPE: DNA
<213> ORGANISM: Artificial Sequence
<220> FEATURE:
<223> OTHER INFORMATION: A2-HRC-F
<220> FEATURE:
<221> NAME/KEY: primer_bind
<222> LOCATION: (1)..(48)

<400> SEQUENCE: 21
agaccttcag caacggcggt ggttctggta acttctacga ccccctgg 48

<210> SEQ ID NO 22
<211> LENGTH: 48
<212> TYPE: DNA
<213> ORGANISM: Artificial Sequence
<220> FEATURE:
<223> OTHER INFORMATION: A2-HRC-R
<220> FEATURE:
<221> NAME/KEY: primer_bind
<222> LOCATION: (1)..(48)

<400> SEQUENCE: 22
ccagggggtc gtagaagtta ccagaaccac cgccgttgct gaaggtct 48

<210> SEQ ID NO 23
<211> LENGTH: 59
<212> TYPE: DNA
<213> ORGANISM: Artificial Sequence
<220> FEATURE:
<223> OTHER INFORMATION: Site0-N-F
<220> FEATURE:
<221> NAME/KEY: primer_bind
<222> LOCATION: (1)..(59)

<400> SEQUENCE: 23
gccggatcca gcaacatcaa ggagaacaag tgcaacgccg ccaagaacta catcgacaa 59

<210> SEQ ID NO 24
<211> LENGTH: 60
<212> TYPE: DNA
<213> ORGANISM: Artificial Sequence
<220> FEATURE:
<223> OTHER INFORMATION: SiteO-C-R
<220> FEATURE:
<221> NAME/KEY: primer_bind
<222> LOCATION: (1)..(60)

<400> SEQUENCE: 24
gccaagcttc ttgttcacga tgggcagcag ctgcttgtcg atgtagttct tggcggcgtt 60

<210> SEQ ID NO 25
<211> LENGTH: 31
<212> TYPE: DNA
<213> ORGANISM: Artificial Sequence
<220> FEATURE:
<223> OTHER INFORMATION: HRN-BamHI-R
<220> FEATURE:
<221> NAME/KEY: primer_bind
<222> LOCATION: (1)..(31)

<400> SEQUENCE: 25
gccggatcca gaaccagaac cgctctgctt g 31

<210> SEQ ID NO 26
<211> LENGTH: 32
<212> TYPE: DNA
<213> ORGANISM: Artificial Sequence
<220> FEATURE:
<223> OTHER INFORMATION: HRC-EcoRI-F
<220> FEATURE:
<221> NAME/KEY: primer_bind
<222> LOCATION: (1)..(32)

<400> SEQUENCE: 26
cggaattcgg tggttctggt aacttctacg ac 32

<210> SEQ ID NO 27
<211> LENGTH: 27
<212> TYPE: DNA
<213> ORGANISM: Artificial Sequence
<220> FEATURE:
<223> OTHER INFORMATION: SiteO-NheI-F
<220> FEATURE:
<221> NAME/KEY: primer_bind
<222> LOCATION: (1)..(27)

<400> SEQUENCE: 27
ctagctagca gcaacatcaa ggagaac 27

<210> SEQ ID NO 28
<211> LENGTH: 34
<212> TYPE: DNA
<213> ORGANISM: Artificial Sequence
<220> FEATURE:
<223> OTHER INFORMATION: SiteO-BamHI-R

```
<220> FEATURE:
<221> NAME/KEY: primer_bind
<222> LOCATION: (1)..(34)

<400> SEQUENCE: 28

gccggatccg cctcccttgt tcacgatggg cagc                                34

<210> SEQ ID NO 29
<211> LENGTH: 27
<212> TYPE: DNA
<213> ORGANISM: Artificial Sequence
<220> FEATURE:
<223> OTHER INFORMATION: SiteO-BamHI-F
<220> FEATURE:
<221> NAME/KEY: primer_bind
<222> LOCATION: (1)..(27)

<400> SEQUENCE: 29

gccggatcca gcaacatcaa ggagaac                                        27

<210> SEQ ID NO 30
<211> LENGTH: 33
<212> TYPE: DNA
<213> ORGANISM: Artificial Sequence
<220> FEATURE:
<223> OTHER INFORMATION: SiteO-EcoRI-R
<220> FEATURE:
<221> NAME/KEY: primer_bind
<222> LOCATION: (1)..(33)

<400> SEQUENCE: 30

cggaattcgc ctcccttgtt cacgatgggc agc                                 33

<210> SEQ ID NO 31
<211> LENGTH: 26
<212> TYPE: DNA
<213> ORGANISM: Artificial Sequence
<220> FEATURE:
<223> OTHER INFORMATION: SiteO-EcoRI-F
<220> FEATURE:
<221> NAME/KEY: primer_bind
<222> LOCATION: (1)..(26)

<400> SEQUENCE: 31

cggaattcag caacatcaag gagaac                                         26

<210> SEQ ID NO 32
<211> LENGTH: 28
<212> TYPE: DNA
<213> ORGANISM: Artificial Sequence
<220> FEATURE:
<223> OTHER INFORMATION: SiteO-HindIII-R
<220> FEATURE:
<221> NAME/KEY: primer_bind
<222> LOCATION: (1)..(28)

<400> SEQUENCE: 32

cccaagcttc ttgttcacga tgggcagc                                       28

<210> SEQ ID NO 33
<211> LENGTH: 27
<212> TYPE: DNA
<213> ORGANISM: Artificial Sequence
<220> FEATURE:
<223> OTHER INFORMATION: HBc148-NcoI-F
```

-continued

```
<220> FEATURE:
<221> NAME/KEY: primer_bind
<222> LOCATION: (1)..(27)

<400> SEQUENCE: 33

ccgccatgga cattgaccct tataaag                                          27


<210> SEQ ID NO 34
<211> LENGTH: 30
<212> TYPE: DNA
<213> ORGANISM: Artificial Sequence
<220> FEATURE:
<223> OTHER INFORMATION: HBc148-XhoI-R
<220> FEATURE:
<221> NAME/KEY: primer_bind
<222> LOCATION: (1)..(30)

<400> SEQUENCE: 34

catgctcgag aacagtagtt tccggaagtg                                       30


<210> SEQ ID NO 35
<211> LENGTH: 21
<212> TYPE: DNA
<213> ORGANISM: Artificial Sequence
<220> FEATURE:
<223> OTHER INFORMATION: RSV-A-N-F730
<220> FEATURE:
<221> NAME/KEY: primer_bind
<222> LOCATION: (1)..(21)

<400> SEQUENCE: 35

gcaggattgt ttatgaatgc c                                                21


<210> SEQ ID NO 36
<211> LENGTH: 20
<212> TYPE: DNA
<213> ORGANISM: Artificial Sequence
<220> FEATURE:
<223> OTHER INFORMATION: RSV-A-N-R857
<220> FEATURE:
<221> NAME/KEY: primer_bind
<222> LOCATION: (1)..(20)

<400> SEQUENCE: 36

tccacaactt gttccatttc                                                  20


<210> SEQ ID NO 37
<211> LENGTH: 22
<212> TYPE: DNA
<213> ORGANISM: Artificial Sequence
<220> FEATURE:
<223> OTHER INFORMATION: CpG

<400> SEQUENCE: 37

tcgtcgtttt cggcgcgcgc cg                                               22
```